(12) United States Patent
Ander et al.

(10) Patent No.: US 10,189,891 B2
(45) Date of Patent: Jan. 29, 2019

(54) AFFINITY CHROMATOGRAPHY MATRIX

(71) Applicant: GE Healthcare BioProcess R&D AB, Uppsala (SE)

(72) Inventors: Mats Ander, Uppsala (SE); Goran Bauren, Uppsala (SE); Tomas Bjorkman, Uppsala (SE); Per-Mikael Aberg, Uppsala (SE); Gustav Rodrigo, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 667 days.

(21) Appl. No.: 14/385,336

(22) PCT Filed: Mar. 26, 2013

(86) PCT No.: PCT/SE2013/050335
§ 371 (c)(1),
(2) Date: Sep. 15, 2014

(87) PCT Pub. No.: WO2013/147691
PCT Pub. Date: Oct. 3, 2013

(65) Prior Publication Data
US 2015/0080554 A1    Mar. 19, 2015

(30) Foreign Application Priority Data

Mar. 28, 2012   (SE) .................... 1250304
May 15, 2012   (SE) .................... 1250493

(51) Int. Cl.
| | |
|---|---|
| C07K 1/22 | (2006.01) |
| C07K 14/31 | (2006.01) |
| C07K 16/00 | (2006.01) |
| B01J 20/286 | (2006.01) |
| B01D 15/38 | (2006.01) |
| B01J 20/291 | (2006.01) |
| G01N 33/68 | (2006.01) |
| B01J 20/32 | (2006.01) |

(52) U.S. Cl.
CPC .......... *C07K 16/00* (2013.01); *B01D 15/3809* (2013.01); *B01J 20/286* (2013.01); *B01J 20/291* (2013.01); *B01J 20/3212* (2013.01); *B01J 20/3219* (2013.01); *B01J 20/3274* (2013.01); *C07K 1/22* (2013.01); *C07K 14/31* (2013.01); *G01N 33/6854* (2013.01); *B01J 2220/80* (2013.01)

(58) Field of Classification Search
None
See application file for complete search history.

(56) References Cited

U.S. PATENT DOCUMENTS

| | | | |
|---|---|---|---|
| 5,143,844 A | 9/1992 | Abrahmsen et al. | |
| 5,580,788 A | 12/1996 | Kihira et al. | |
| 6,399,750 B1 | 6/2002 | Johansson | |
| 6,602,977 B1 | 8/2003 | Ljungqvist et al. | |
| 6,602,990 B1 | 8/2003 | Berg | |
| 7,396,467 B2 | 7/2008 | Berg et al. | |
| 7,709,209 B2 | 5/2010 | Hober et al. | |
| 7,951,885 B2 * | 5/2011 | Joehnck | B01J 20/26 526/310 |
| 7,993,848 B2 | 8/2011 | Herne | |
| 2005/0143566 A1 | 6/2005 | Hober | |
| 2006/0194950 A1 | 8/2006 | Hober et al. | |
| 2006/0194955 A1 | 8/2006 | Hober et al. | |
| 2008/0167450 A1 | 7/2008 | Pan | |
| 2010/0080065 A1 | 4/2010 | Fujiki et al. | |
| 2013/0096276 A1 | 4/2013 | Yoshida et al. | |
| 2013/0274451 A1 * | 10/2013 | Bjorkman | B01D 15/3809 530/389.5 |
| 2013/0338339 A1 * | 12/2013 | Bjorkman | B01D 15/168 530/324 |

FOREIGN PATENT DOCUMENTS

| | | |
|---|---|---|
| EP | 0230869 B1 | 9/1992 |
| EP | 0550771 B1 | 9/1999 |
| EP | 0873353 B1 | 7/2003 |
| EP | 1485407 B1 | 5/2009 |
| EP | 1869071 B1 | 12/2010 |

(Continued)

OTHER PUBLICATIONS

European Search Report dated Mar. 3, 2016 in corresponding European Application No. 13767846.2.
Ejima, D., et al., Analytical Biochemistry, 345 (2005) 250-257.
International Preliminary Report on Patentability received for PCT Patent Application No. PCT/SE2013/050335 dated Oct. 1, 2014, 10 pages.
International Search opinion and Written Opinion received for PCT Application No. PCT/SE2013/050335 dated Jul. 19, 2013, 16 pages.

(Continued)

*Primary Examiner* — Daniel E Kolker
*Assistant Examiner* — James L Rogers
(74) *Attorney, Agent, or Firm* — Wood IP LLC

(57) ABSTRACT

The invention discloses an immunoglobulin-binding protein comprising one or more mutated immunoglobulin-binding domains (monomers) of staphylococcal Protein A (E, D, A, B, C) or protein Z or a functional variant thereof, wherein in at least one of the one or more mutated monomers, the asparagine or histidine at the position corresponding to H18 of the B domain of Protein A or of Protein Z has been deleted or substituted with a first amino acid residue which is not proline or asparagine and wherein, if the amino acid residue at position 57 is proline and the amino acid residue at position 28 is asparagine, then the amino acid residue at the position corresponding to H18 of the B domain of protein A or of protein Z is not serine, threonine or lysine.

40 Claims, 4 Drawing Sheets
Specification includes a Sequence Listing.

(56) References Cited

FOREIGN PATENT DOCUMENTS

| | | | |
|---|---|---|---|
| EP | 2557157 A1 | 2/2013 | |
| EP | 2831096 A1 | 2/2015 | |
| JP | 62-190087 A | 8/1987 | |
| JP | 0532699 A | 2/1993 | |
| JP | 2005-538693 A | 12/2005 | |
| JP | 4117903 B2 | 7/2008 | |
| JP | 5462461 B2 | 4/2014 | |
| JP | 5952185 B2 | 7/2016 | |
| WO | 93/02107 A1 | 2/1993 | |
| WO | 1997/017361 A1 | 5/1997 | |
| WO | WO 2003/080655 | 10/2003 | |
| WO | WO 2005/003156 | 1/2005 | |
| WO | WO 2005/075507 | 8/2005 | |
| WO | WO 2006/092338 | 9/2006 | |
| WO | WO 2007019376 A2 * | 2/2007 | ........... A61K 49/085 |
| WO | WO 20081039141 | 4/2008 | |
| WO | WO 2010080065 A1 * | 7/2010 | ......... B01D 15/3809 |
| WO | WO 2011/028753 | 3/2011 | |
| WO | 2011/118699 A1 | 9/2011 | |
| WO | 2012087231 A1 | 6/2012 | |
| WO | 2013/147691 A1 | 10/2013 | |

OTHER PUBLICATIONS

Office Action received for Japanese Patent Application No. 2015-503160, dated Jan. 10, 2017, 11 pages. (Official Copy Only).

Office Action Received for European Patent Application No. 13767846.2, dated Sep. 9, 2016, 7 pages.

Japan Notice of Preliminary Rejection for Japanese Patent Application No. 2015503160, dated Sep. 5, 2017, 4 pages.

Hjertén, "The Preparation of Agarose Spheres for Chromatography of Molecules and Particles", Biochimica et Biophysica Acta, vol. 79, No. 2, 1964, pp. 393-398.

Deisenhofer, "Crystallographic Refinement and Atomic Models of a Human Fc Fragment and its Complex with Fragment B of Protein A from Staphylococcus Aureus at 2.9- and 2.8-.Ang. Resolution", Biochemistry, vol. 20, No. 9, 1981, pp. 2361-2370.

Arshady, "Styrene Based Polymer Supports Developed by Suspension Polymerization", La Chimica E L'Industria, vol. 70 No. 9, 1988, pp. 70-75.

Graille et al. "Crystal Structure of a Staphylococcus Aureus Protein A Domain Complexed With the Fab Fragment of a Human IgM Antibody: Structural Basis for Recognition of B-cell Receptors and Superantigen activity", PNAS, vol. 97, No. 10, 2000, pp. 5399-5404.

Gulich et al. "Stability Towards Alkaline Conditions Can be Engineered Into a Protein Ligand", Journal of Biotechnology, vol. 80, 2000, pp. 169-178.

Wilchek et al. "An Overview of Affinity Chromatography", Methods in Molecular Biology, vol. 147, 2002, pp. 1-6.

Stahl, "Affinity Fusions, Gene Expression", Encyclopedia of Bioprocess Technology, 2002, pp. 8-22.

Ghose, "Antibody Variable Region Interactions With Protein A: Implications for the Development of Generic Purification Processes", Biotechnology and Bioengineering, vol. 92, No. 6, 2005, pp. 665-673.

* cited by examiner

Protein A (five domains, EDABC)

(N-terminus)

```
              < Helix 1>       < Helix 2 >        < Helix 3 >
              QQNAFYQVLNMPNLNADQRNGFIQSLKDDPSQSANVLGEAQKLNDSQAPK  (E) SEQ ID No: 1
ADAQQNNFNKDQQSAFYEILNMPNLNEAQRNGFIQSLKDDPSQSTNVLGEAKKLNESQAPK  (D) SEQ ID No: 2
ADNNFNKEQQNAFYEILNMPNLNEEQRNGFIQSLKDDPSQSANLLSEAKKLNESQAPK    (A) SEQ ID No: 3
ADNKFNKEQQNAFYEILHLPNLNEEQRNGFIQSLKDDPSQSANLLAEAKKLNDAQAPK    (B) SEQ ID No: 4
ADNKFNKEQQNAFYEILHLPNLTEEQRNGFIQSLKDDPSVSKEILAEAKKLNDAQAPK    (C) SEQ ID No: 5
                                                              (C-terminus)

VDNKFNKEQQNAFYEILHLPNLNEEQRNAFIQSLKDDPSQSANLLAEAKKLNDAQAPK    (Z)  SEQ ID No:6
VDNKFNKEQQNAFYEILHLPNLTEEQRNAFIQSLKDDPSQSKEILAEAKKLNDAQAPK    (Zv) SEQ ID No:7
VDAKFDKEQQNAFYEILHLPNLTEEQRNAFIQSLKDDPSQSKEILAEAKKLNDAQAPK    (Zv2)SEQ ID No:8
```

Figure 1

AFFINITY CHROMATOGRAPHY MATRIX

CROSS-REFERENCE TO RELATED APPLICATIONS

This application is a filing under 35 U.S.C. 371 of international application number PCT/SE2013/050335, filed Mar. 26, 2013, published on Oct. 3, 2013 as WO 2013/147691, which claims priority to application numbers 1250304-1 filed in Sweden on Mar. 28, 2012 and 1250493-2 filed in Sweden on May 15, 2012.

FIELD OF THE INVENTION

The present invention relates to the field of affinity chromatography, and more specifically to separation matrices containing ligands with one or more of a protein A domain (E, D, A, B, C), or protein Z, which have been mutated. The invention also relates to methods for the separation of proteins of interest on such separation matrices.

BACKGROUND OF THE INVENTION

Immunoglobulins, in particular monoclonal antibodies (mAbs) represent the most prevalent biopharmaceutical products in either manufacture or development worldwide. The high commercial demand for and hence value of this particular therapeutic market has led to the intense efforts from pharmaceutical companies to maximise the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection. At present, SpA-based affinity medium probably is the most widely used affinity medium for isolation of monoclonal antibodies and their fragments from different samples including industrial feed stocks from cell cultures. Accordingly, various matrices comprising protein A ligands are commercially available, for example, in the form of native protein A (e.g. Protein A SEPHAROSE™, GE Healthcare, Uppsala, Sweden) and also comprised of recombinant protein A (e.g. rProtein A SEPHAROSE™, GE Healthcare). More specifically, the genetic manipulation performed in the commercial recombinant protein A product is aimed at facilitating the attachment thereof to a support.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitising agent is NaOH, and the concentration thereof can range from 0.1 up to e.g. 1 M, depending on the degree and nature of contamination. This strategy is associated with exposing the matrix for pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focussed on the development of engineered protein ligands that exhibit an improved capacity to withstand alkaline pH-values. For example, Gülich et al (Journal of Biotechnology 80 (2000), 169-178) suggested protein engineering to improve the stability properties of a Streptococcal albumin-binding domain (ABD) in alkaline environments. Gülich et al created a mutant of ABD, wherein all the four asparagine residues have been replaced by leucine (one residue), aspartate (two residues) and lysine (one residue). Further, Gülich et al report that their mutant exhibits a target protein binding behaviour similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work show that changes can also be made to protein A (SpA) to effect similar properties. US patent application 2005/0143566 discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844). The authors show that when these mutated proteins are used as affinity ligands, the separation media as expected can better withstand cleaning procedures using alkaline agents. US patent application 2006/0194955 shows that the mutated ligands can better withstand proteases thus reducing ligand leakage in the separation process. Another US patent application 2006/0194950 shows that the alkali stable SpA domains can be further modified such that the ligands lacks affinity for Fab but retains Fc affinity, for example by a G29A mutation.

Historically the native protein A containing 5 IgG binding domains was used for production of all protein A affinity media. Using recombinant technology a number of protein A construct have been produced all containing 4 or 5 IgG binding domains. A recent study shows that dimeric ligands have a similar, or increased binding capacity compared to tetrameric ligands (WO 2010/080065).

It is well known that some antibodies are prone to aggregation or sensitive (e.g. they can lose activity) at low pH. There is still a need in this field to obtain a separation matrix containing protein ligands having an increased elution pH for antibody or related targets. Further there is a need for improved selectivity in the initial capture step of mAb processes, leading to improved clearance of host cell proteins and antibody aggregates.

SUMMARY OF THE INVENTION

A first aspect of the invention is to provide a mutated immunoglobulin- or Fc-binding protein with improved dissociation properties, including release of bound immunoglobulins or Fc-containing proteins at an increased pH and selective release of monomeric immunoglobulins or Fc-containing proteins at pH values higher than for bound host cell proteins and/or aggregates of immunoglobulins or Fc-containing proteins. This is achieved with a mutated immunoglobulin- or Fc-binding protein as defined in Claim 1.

A second aspect of the present invention is to provide an affinity separation matrix with improved elution properties, including elution of bound immunoglobulins or Fc-containing proteins at an increased pH and selective elution of monomeric immunoglobulins or Fc-containing proteins at pH values higher than for bound host cell proteins and/or aggregates of immunoglobulins or Fc-containing proteins. This is achieved with an affinity separation matrix as defined in Claim 9.

A third aspect of the invention is to provide a method for separating one or more Fc-containing proteins, which method allows elution of bound Fc-containing proteins at an increased pH and selective elution of monomeric Fc-containing proteins at pH values higher than for bound host cell proteins and/or aggregates of Fc-containing proteins. This is achieved with a method according to Claim 16.

A fourth aspect of the invention is to provide a method of selecting an elution buffer for matrices with adsorbed Fc-containing proteins, which method allows for selection of buffers allowing selective elution of monomeric Fc-containing proteins at pH values higher than for bound host cell proteins and/or aggregates of Fc-containing proteins. This is achieved with a method according to Claim 28.

Further suitable embodiments of the invention are described in the depending claims.

BRIEF DESCRIPTION OF THE DRAWINGS

FIG. 1 shows an alignment of the amino acid sequences from each of the five domains of protein A, along with three varieties of protein Z. The Asparagine or Histidine at the position corresponding to H18 of B domain of Protein A is denoted in bold. Also shown are the locations of the three alpha-helices (Graille et al, PNAS 2000, 97 (10): 5399-5404; Deisenhofer, Biochemistry 1981, 20 (9): 2361-2370).

DETAILED DESCRIPTION OF THE INVENTION

Definitions

Figure 2:
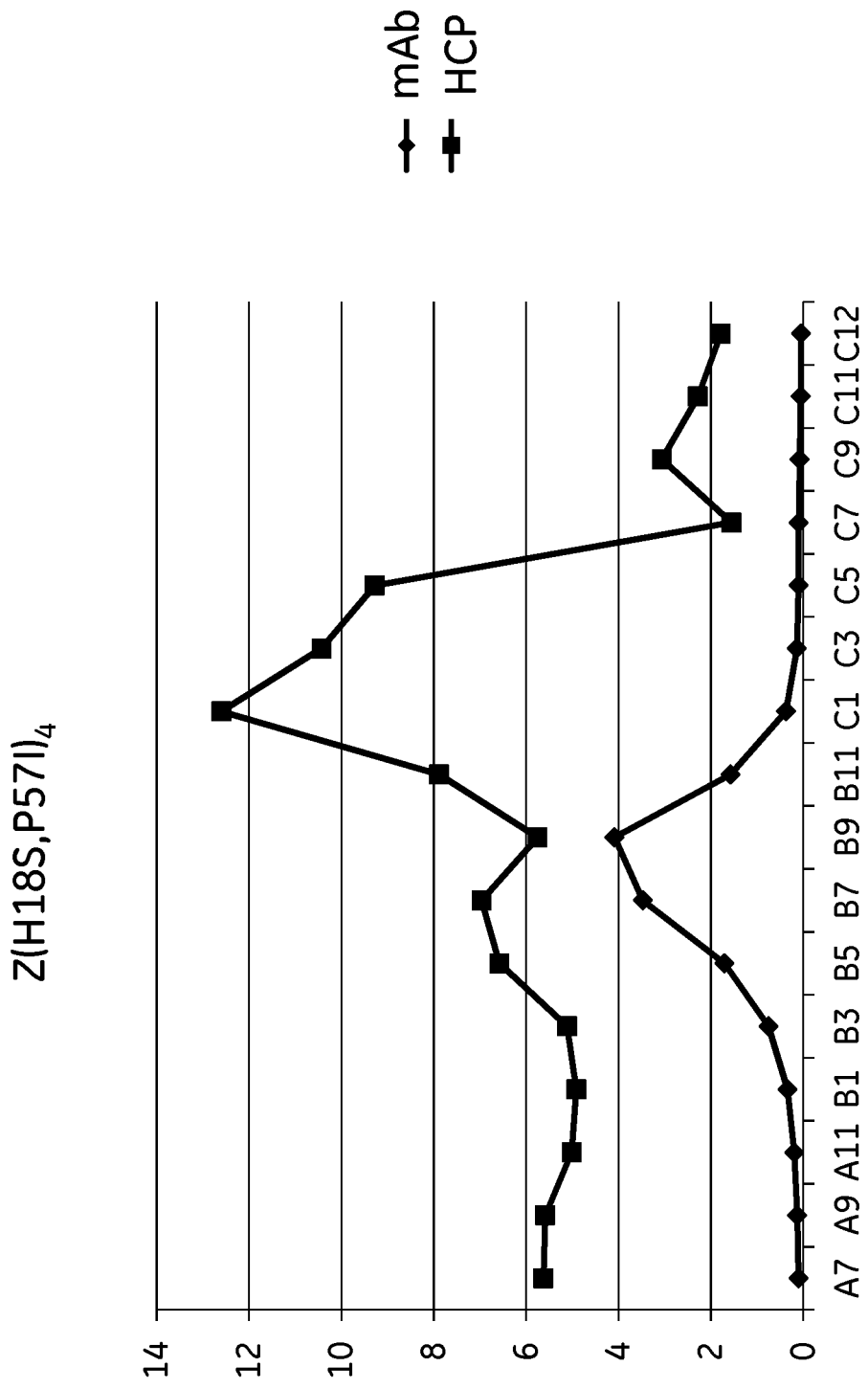
FIG. 2 shows an overlay of the pH-gradient elution chromatograms of monoclonal antibody and host cell proteins for prototype Z(H18S,P57I)4.

The term "protein" is used herein to describe proteins as well as fragments thereof. Thus, any chain of amino acids that exhibits a three dimensional structure is included in the term "protein", and protein fragments are accordingly embraced.

The term "functional variant" of a protein means herein a variant protein, wherein the function, in relation to the invention defined as affinity and stability, are essentially retained. Thus, one or more amino acids that are not relevant for said function may have been exchanged.

The term "parental molecule" is used herein for the corresponding protein in the form before a mutation according to the invention has been introduced.

The term "structural stability" refers to the integrity of three-dimensional form of a molecule, while "chemical stability" refers to the ability to withstand chemical degradation.

The term "Fc-binding" protein means that the protein is capable of binding to the Fc (also called "fragment, crystallisable") region of an immunoglobulin. However, it is not excluded that an Fc-binding protein also can bind other regions, such as Fab regions of immunoglobulins.

The term "Fc-containing protein" means a protein comprising an Fc region or fragment of an immunoglobulin. The Fc-containing protein can be an immunoglobulin or a fusion protein or conjugate comprising an Fc region/fragment or comprising an entire immunoglobulin.

In the present specification, if not referred to by their full names, amino acids are denoted with the conventional one-letter or three letter symbols.

Mutations are defined herein by the number of the position exchanged, preceded by the wild type or non-mutated amino acid and followed by the mutated amino acid. Thus, for example, the mutation of a histidine (H) in position 18 to a glutamic acid (E) is denoted H18E. Deletion mutations are defined by the number of the position deleted, preceded by the wild-type or non-mutated amino acid and followed by "del". Thus, for example, the deletion of a histidine in position 18 is denoted H18del.

In a first aspect the present invention discloses an immunoglobulin- or Fc-binding protein which comprises one or more mutated immunoglobulin- or Fc-binding domains (also called monomers) of staphylococcal Protein A (i.e. the E, D, A, B and/or C domains) or protein Z or a functional variant thereof, such as the variants defined by SEQ ID NO: 7 or SEQ ID NO: 8. In at least one of the one or more mutated monomers, the Asparagine or Histidine at the position corresponding to H18 of the B domain of Protein A (SEQ ID NO:4) or of Protein Z (SEQ ID NO:6) has been substituted with a first amino acid residue which is not Proline or Asparagine. Further, if the amino acid residue at the position corresponding to P57 of the B domain of Protein A or of Protein Z is Proline and the amino acid residue at the position corresponding to N28 of the B domain of Protein A or of Protein Z is Asparagine, then the amino acid residue at the position corresponding to H18 of the B domain of Protein A or of Protein Z is not Serine, Threonine or Lysine. An advantage of this mutated protein is that it binds immunoglobulins and Fc-containing proteins and releases them at pH levels higher than immunoglobulin- or Fc-binding proteins not having the H18 mutation. The mutation of the Asparagine or Histidine residue at the position corresponding to H18 of B domain of Protein A or Protein Z unexpectedly increases the elution pH of immunoglobulins and Fc-containing proteins, such as IgG, IgA and/or IgM, or fusion proteins containing an Fc-fragment. Preferably, the elution pH increases by between 0.2 to over 1.0 pH. More preferably, the elution pH increases at least 0.3 pH, most preferably, the elution pH increases at least 0.4 pH. Alternatively, the elution pH is increased to >4.0, preferably pH>4.2, while the yield of the target molecule is at least 80% or preferably >95%. As immunoglobulins and other Fc-containing proteins are prone to aggregation at low pH levels, this is important for the use of the proteins in bioprocessing. The aggregates are potentially immunogenic and need to be removed before pharmaceutical use of the immunoglobulins or Fc-containing proteins. This adds significant cost to the processing.

A further advantage of the mutation of the Asparagine or Histidine residue at the position corresponding to H18 of B domain of Protein A or Protein Z is that any host cell proteins (HCP) or aggregates of antibodies or Fc-containing proteins that adsorb to the matrix will elute at a higher pH than the antibody/Fc-containing protein monomers. It is then possible to recover the monomeric antibody or FC-containing protein at a higher purity by eluting it at a pH where HCP and aggregates are still bound to the matrix. On comparative matrices with ligands not having the H18 mutations, bound HCP and aggregates coelute with the antibody monomers.

In certain embodiments, the ligands are also rendered alkali-stable, such as by mutating at least one asparagine residue of at least one of the monomeric domains of the SpA domain B or protein Z to an amino acid other than glutamine. As discussed earlier, US patent application 2005/0143566 discloses that when at least one asparagine residue is mutated to an amino acid other than glutamine or aspartic acid, the mutation confers the ligand an increased chemical stability at high pH (e.g., N23T). Further, affinity media including these ligands can better withstand cleaning procedures using alkaline agents. US patent application 2006/0194955 shows that the mutated ligands can also better withstand proteases thus reducing ligand leakage in the separation process. The disclosures of these applications are hereby incorporated by reference in their entirety.

In some embodiments, the ligand(s) so prepared lack any substantial affinity for the Fab part/region of an antibody, while having affinity for the Fc part/region. Thus, in certain embodiments, at least one glycine of the ligands has been replaced by an alanine. US patent application 2006/0194950 shows that the alkali stable domains can be further modified such that the ligands lacks affinity for Fab but retains Fc affinity, for example by a G29A mutation. The disclosure of the application is hereby incorporated by reference in its entirety. The numbering used herein of the amino acids is the conventionally used in this field, exemplified by the position on domain B of protein A, and the skilled person in this field can easily recognize the position to be mutated for each domain of E, D, A, B, C.

In certain embodiments, an asparagine residue located between a leucine residue and a glutamine residue has also been mutated, for example to a threonine residue. Thus, in one embodiment, the asparagine residue in position 23 of the sequence defined in SEQ ID NO: 6 has been mutated, for example to a threonine residue. In a specific embodiment, the asparagine residue in position 43 of the sequence defined in SEQ ID NO: 6 has also been mutated, for example to a glutamic acid. In the embodiments where amino acid number 43 has been mutated, it appears to most advantageously be combined with at least one further mutation, such as N23T.

Accordingly, in some embodiments, a mutated protein according to the invention comprises at least about 75%, such as at least about 80% or preferably at least about 95%, of the sequence as defined in SEQ ID NO: 4 or 6, with the proviso that the asparagine mutation is not in position 21.

In the present specification, SEQ ID NO: 4 defines the amino acid sequence of the B-domain of SpA: ADNKF-NKEQQNAFYEILHLPNLNEEQRNGFIQSLKDDP-SQSANLLAEAKKLNDAQAPK SEQ ID NO: 6 defines a protein known as protein Z: VDNKFNKEQQNAFYEIL-HLPNLNEEQRNAFIQSLKDDPSQSANLLAEAK-KLNDA QAPK Protein Z is a synthetic construct derived from the B-domain of SpA, wherein the glycine in position 29 has been exchanged for alanine, see e.g. Stahl et al, 1999: Affinity fusions in biotechnology: focus on protein A and protein G, in The Encyclopedia of Bioprocess Technology: Fermentation, Biocatalysis and Bioseparation. M. C. Fleckinger and S. W. Drew, editors. John Wiley and Sons Inc., New York, 8-22.

In one embodiment, the above described mutant protein is comprised of the amino acid sequence defined in SEQ ID NO: 4, 5, 6, 7 or 8, or is a functional variant thereof, with a substitution at Histidine at the position corresponding to H18 of B domain of Protein A or Protein Z. In another embodiment, the above described mutant protein is comprised of the amino acid sequence defined in SEQ ID NO: 1, 2 or 3, or is a functional variant thereof, with a substitution at Asparagine at the position corresponding to H18 of B domain of Protein A. The term "functional variant" as used in this context includes any similar sequence, which comprises one or more further variations in amino acid positions that have no influence on the mutant protein's affinity to immunoglobulins or Fc-containing proteins or its improved chemical stability in environments of increased pH-values.

As mentioned above, in order to achieve a mutant protein useful as a ligand with high binding capacity for a prolonged period of time in alkaline conditions, mutation of the asparagine residue in position 21 is avoided. In one embodiment, the asparagine residue in position 3 is not mutated.

As the skilled person in this field will easily understand, the mutation of Asparagine or Histidine at position 18, the mutations at positions 57 and 28, the mutations to provide alkaline-stability, and the G to A mutation may be carried out in any order of sequence using conventional molecular biology techniques. Further, the ligands can be expressed by a vector containing a nucleic acid sequence encoding the mutated protein ligands. Alternatively, they can also be made by protein synthesis techniques. Methods for synthesizing peptides and proteins of predetermined sequences are well known and commonly available in this field.

In certain embodiments, amino acids with bulky side chains, e.g. Tyrosine, Tryptophan or Methionine can be avoided as substituents in the H18 position. Bulky side chains may perturb the tertiary structure of the protein, which could affect the immunoglobulin- or Fc-binding properties.

In some embodiments additionally at least one of the Proline at position 57 and the Asparagine at position 28 has been substituted with a second amino acid residue. An advantage of this is that even higher elution pH values can be achieved, in combination with higher binding capacities. In certain embodiments neither of the amino acid residues at positions 57 and 28 is Proline or Asparagine.

In some embodiments the amino acid residue at position 18 is selected from the group consisting of Serine, Glutamic acid, Aspartic acid, Threonine and Lysine. With these amino acids, particularly high elution pH levels can be achieved.

In certain embodiments at least one of the amino acid residues at position 57 and 28 is selected from the group consisting of Alanine and Isoleucine.

In some embodiments the protein comprises one or more mutated monomers derived from the parental molecules defined by SEQ ID NO 5, 6, 7 or 8, wherein the mutation is selected from the group consisting of H18E; H18S,N28A; H18S,P57I; N28A,P57I and H18S,N28A,P57I.

In certain embodiments the protein comprises one or more mutated monomers defined by SEQ ID NO: 14, 16, 17 or 18.

In some embodiments the protein comprises at least two mutated monomers, such as 3, 4, 5 or 6 monomers, forming a multimeric protein. The monomers may be linked covalently, such as by forming parts of a single polypeptide chain. The mutated monomers may be identical, but they can also be different mutated monomers according to the invention. In addition to the monomers of the invention, the multimeric protein may also comprise other mutated or non-mutated IgG-binding domains of Protein A. In some embodiments the Asparagine or Histidine at the position corresponding to H18 of B domain of Protein A or Protein Z in at least one of the monomeric domains in a multimeric ligand is substituted. In other embodiments, the Asparagine or Histidine residue in all the monomeric domains in a multimeric ligand is substituted.

In some embodiments, the multimeric protein according to the invention comprises monomer units linked to each other by a stretch of amino acids preferably ranging from 0 to 15 amino acids, such as 0-5, 0-10 or 5-10 amino acids. The nature of such a link should preferably not destabilize the spatial conformation of the protein units. This can e.g. be achieved by avoiding the presence of proline in the links. Furthermore, said link should preferably also be sufficiently stable in alkaline environments not to impair the properties of the mutated protein units. For this purpose, it is advantageous if the links do not contain asparagine. It can additionally be advantageous if the links do not contain glutamine.

In certain embodiments, the present dimeric ligands comprise the sequence of SEQ ID NO: 9:

VDAKFDKEQQNAFYEILELPNLTEEQRNAFIQSLKDDPSQSANLLAEAK

KLNDAQAPKVDAKFDKEQQNAFYEILELPNLTEEQRNAFIQSLKDDPSQ

SANLLAEAKKLNDAQAPKC

In certain embodiments, the present tetrameric ligands comprise the sequence of SEQ ID NO: 11:

VDAKFDKEQQNAFYEILSLPNLTEEQRNAFIQSLKDDPSQSANLLAEAK

KLNDAQAIKVDAKFDKEQQNAFYEILSLPNLTEEQRNAFIQSLKDDPSQ

SANLLAEAKKLNDAQAIKVDAKFDKEQQNAFYEILSLPNLTEEQRNAFI

QSLKDDPSQSANLLAEAKKLNDAQAIKVDAKFDKEQQNAFYEILSLPNL

TEEQRNAFIQSLKDDPSQSANLLAEAKKLNDAQAIKC

In some embodiments, the present tetrameric ligands comprise the sequence of SEQ ID NO: 12:

VDAKFDKEQQNAFYEILSLPNLTEEQRAAFIQSLKDDPSQSANLLAEAK

KLNDAQAPKVDAKFDKEQQNAFYEILSLPNLTEEQRAAFIQSLKDDPSQ

SANLLAEAKKLNDAQAPKVDAKFDKEQQNAFYEILSLPNLTEEQRAAFI

QSLKDDPSQSANLLAEAKKLNDAQAPKVDAKFDKEQQNAFYEILSLPNLT

EEQRAAFIQSLKDDPSQSANLLAEAKKLNDAQAPKC

In certain embodiments, the present tetrameric ligands comprise the sequence of SEQ ID NO: 13:

VDAKFDKEQQNAFYEILSLPNLTEEQRAAFIQSLKDDPSQSANLLAEAK

KLNDAQAIKVDAKFDKEQQNAFYEILSLPNLTEEQRAAFIQSLKDDPSQ

SANLLAEAKKLNDAQAIKVDAKFDKEQQNAFYEILSLPNLTEEQRAAFI

QSLKDDPSQSANLLAEAKKLNDAQAIKVDAKFDKEQQNAFYEILSLPNLT

EEQRAAFIQSLKDDPSQSANLLAEAKKLNDAQAIKC

In certain embodiments the protein further comprises a C-terminal cysteine. The cysteine can be directly linked to the C-terminal monomer of a protein according to the invention or it can also be linked via a stretch of amino acids preferably ranging from 0 to 15 amino acids, such as 0-5, 0-10 or 5-10 amino acids. This stretch should preferably also be sufficiently stable in alkaline environments not to impair the properties of the mutated protein. For this purpose, it is advantageous if the stretch does not contain asparagine. It can additionally be advantageous if the stretch does not contain glutamine. An advantage of having a C-terminal cysteine is that endpoint coupling of the protein can be achieved through reaction of the cysteine thiol with an electrophilic group on a support. This provides excellent mobility of the coupled protein which is important for the binding capacity.

In a second aspect the invention discloses an affinity separation matrix, which comprises a protein according to any of the embodiments described above coupled to a support. This matrix is useful for chromatographic separation of immunoglobulins and other Fc-containing proteins, where the higher elution pH and the improved elution selectivity allow for better recoveries and lower impurity levels after the first capture step.

As the skilled person will understand, the expressed protein should be purified to an appropriate extent before been immobilized to a support. Such purification methods are well known in the field, and the immobilization of protein-based ligands to supports is easily carried out using standard methods. Suitable methods and supports will be discussed below in more detail.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N— substituted forms), amino (—NH$_2$, possibly in substituted form), oligo- or polyethylenoxy groups on their external and, if present, also on internal surfaces.

The ligand may be attached to the support via conventional coupling techniques utilising, e.g. amino and/or carboxy groups present in the ligand. Bisepoxides, epichlorohydrin, CNBr, N-hydroxysuccinimide (NHS) etc are well-known coupling reagents. Between the support and the ligand, a molecule known as a spacer can be introduced, which improves the availability of the ligand and facilitates the chemical coupling of the ligand to the support. Alternatively, the ligand may be attached to the support by non-covalent bonding, such as physical adsorption or biospecific adsorption.

In some embodiments the matrix comprises 5-15 mg/ml, such as 6-11 mg/ml of said protein coupled to said support. The amount of coupled protein can be controlled by the concentration of protein used in the coupling process, by the coupling conditions used and by the pore structure of the support used. As a general rule the absolute binding capacity of the matrix increases with the amount of coupled protein, at least up to a point where the pores become significantly constricted by the coupled protein. The relative binding capacity per mg coupled protein will decrease at high coupling levels, resulting in a cost-benefit optimum within the ranges specified above.

In certain embodiments the protein is coupled to the support via a thioether bridge.

Methods for performing such coupling are well-known in this field and easily performed by the skilled person in this field using standard techniques and equipment.

In some embodiments the protein is coupled via a C-terminal cysteine provided on the protein as described above. This allows for efficient coupling of the cysteine thiol to electrophilic groups, e.g. epoxide groups, halohydrin groups etc. on a support, resulting in a thioether bridge coupling.

In certain embodiments the support comprises a polyhydroxy polymer, such as a polysaccharide. Examples of polysaccharides include e.g. dextran, starch, cellulose, pullulan, agar, agarose etc. Polysaccharides are inherently hydrophilic with low degrees of nonspecific interactions, they provide a high content of reactive (activatable) hydroxyl groups and they are generally stable towards alkaline cleaning solutions used in bioprocessing.

In some embodiments the support comprises agar or agarose. The supports used in the present invention can easily be prepared according to standard methods, such as inverse suspension gelation (S Hjertén: Biochim Biophys Acta 79(2), 393-398 (1964). Alternatively, the base matrices are commercially available products, such as SEPHAROSE™ FF (GE Healthcare). In an embodiment, which is especially advantageous for large-scale separations, the support has been adapted to increase its rigidity using the methods described in U.S. Pat. No. 6,602,990 or U.S. Pat. No. 7,396,467, and hence renders the matrix more suitable for high flow rates.

In certain embodiments the support is crosslinked, such as with hydroxyalkyl ether crosslinks. Crosslinker reagents producing such crosslinks can be e.g. epihalohydrins like epichlorohydrin, diepoxides like butanediol diglycidyl ether, allylating reagents like allyl halides or allyl glycidyl ether. Crosslinking is beneficial for the rigidity of the support and improves the chemical stability. Hydroxyalkyl ether crosslinks are alkali stable and do not cause significant nonspecific adsorption.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used. In another alternative, the solid support according to the invention comprises a support of inorganic nature, e.g. silica, zirconium oxide etc.

In yet another embodiment, the solid support is in another form such as a surface, a chip, capillaries, or a filter.

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

In a third aspect the present invention relates to a method of separating Fc-containing proteins from other substances, comprising the steps of:
  a) providing an affinity separation matrix according to any of the embodiments described above;
  b) providing a solution comprising an Fc-containing protein and at least one other substance;
  c) contacting said solution with said separation matrix;
  d) optionally washing said separation matrix with at least one wash buffer;
  e) eluting said separation matrix with an elution buffer, or an elution buffer gradient of decreasing pH, to obtain an eluate comprising said Fc-containing protein and;
  f) recovering said eluate.

If an elution buffer with essentially constant pH is used (step elution), the elution buffer has a pH of 4.0-6.0 and if an elution buffer gradient is used (gradient elution) at least part of the elution buffer gradient is within the pH range of 6.0-4.0.

Regular protein A media based on native or recombinant protein A (e.g. MABSELECT™ and rProtein A SEPHAROSE™ 4 Fast Flow) normally elute at pH 3.1-4.0 (measured at peak apex) mainly depending on its VH3 binding (see e.g. Ghose, S. et al. Biotechnology and Bioengineering 92 665-673 [2005]). The alkaline stabilized product MABSELECT SURE™, derived from the B-domain of protein A, essentially lacks the VH3 binding giving a higher elution pH: 3.7-4.0. For a general review of the principles of affinity chromatography, see e.g. Wilchek, M., and Chaiken, I. 2000. An overview of affinity chromatography. Methods Mol. Biol. 147: 1-6.

The substitution of the Asparagine or Histidine residue at the position corresponding to H18 of B domain of Protein A or Protein Z unexpectedly increases the elution pH of immunoglobulins, or fusion proteins containing an Fc-fragment. The substitution thus provides a ligand which allows for elution above pH 4.0, preferably above 4.2, while the yield of target molecule is at least 80% or preferably >95%. This results in gentler elution conditions which minimize the risk for aggregation or inactivation of the target molecule.

Aggregate separation from monomers has been a challenge in antibody purification, especially at higher resolution. The present ligands show an improved separation between monomers and aggregates, making this a viable approach for aggregate removal in the capture step, even at large scale (see FIGS. 5 and 6). It is also possible to remove other contaminants with the method of the invention, such as e.g. DNA, non-desirable antibody isoforms (including certain charge isoforms and glycoforms), endotoxins, viruses, fermentation additives (e.g. antibiotics) etc.

In certain embodiments of the invention, the conditions for the adsorption step may be any conventionally used, appropriately adapted depending on the properties of the target antibody such as the pI thereof. The optional wash step can be performed using a buffer commonly used such as a PBS buffer. It may also be performed with more than one wash buffer, e.g. of different pH, ionic strength or additives. Additives like solvents, salts or detergents or mixtures thereof may be used in one or more wash buffers.

The present method is useful to capture target antibodies, such as a first step in a purification protocol of antibodies which are e.g. for therapeutic or diagnostic use. In one embodiment, at least 75% of the antibodies are recovered. In an advantageous embodiment, at least 80%, such as at least 90%, and preferably at least 95% of the antibodies are recovered using an eluent having a suitable pH for the particular ligand system. Thus, in a specific embodiment, more than about 98% of the antibodies are recovered. The present method may be followed by one or more additional steps, such as other chromatography steps. The additional step(s) may comprise e.g. cation exchange chromatography, anion exchange chromatography, multimodal chromatography (with either positively or negatively charged matrices), thiophilic chromatography, hydroxyapatite chromatography and/or gel filtration. Additional chromatography steps can be performed in either bind-elute or flow-through mode and they can be performed in packed beds or with membrane adsorbers or monolithic columns Hold tanks may or may not be used between steps and it is possible to use e.g. in-line conditioning in order to avoid hold tanks between steps.

In some embodiments the method further comprises a step g) of stripping said separation matrix with a stripping buffer having a pH of a least 0.1 pH units lower than the pH of the elution buffer or the pH of the elution buffer gradient at the end of step e). When the bound host cell proteins, aggregates and other impurities elute at a lower pH, a low pH stripping will efficiently remove these substances from the matrix. Even if an alkaline cleaning step is applied afterwards to remove further impurities, the low pH strip can increase the efficiency of the alkaline cleaning and may prevent any fouling during the alkaline step.

In certain embodiments the solution comprising an Fc-containing protein and at least one other substance comprises host cell proteins (HCP), such as CHO cell or *E Coli* proteins. Contents of CHO cell and *E Coli* proteins can conveniently be determined by immunoassays directed towards these proteins, e.g. the CHO HCP or *E Coli* HCP ELISA kits from Cygnus Technologies.

In some embodiments the host cell proteins or CHO cell/E *Coli* proteins are desorbed during step g).

In certain embodiments the solution comprising an Fc-containing protein and at least one other substance comprises aggregates of said Fc-containing protein, such as at least 1%, at least 5% or at least 10% aggregates calculated on the total amount of the Fc-containing protein in said solution. In many cases an antibody or other Fc-containing protein contains aggregates already in the fermentation broth. The presence of significant aggregate amounts creates major difficulties during the subsequent purification and it is an advantage of the invention that aggregates can be removed directly in the capture step. Aggregate levels can conveniently be determined e.g. by analytical gel filtration, where aggregates elute before the monomeric Fc-containing protein.

In some embodiments aggregates are desorbed during step g).

In certain embodiments the aggregate content in the recovered eluate is less than 1%, such as less than 0.5% or less than 0.2% aggregates calculated on the total amount of the Fc-containing protein in said recovered eluate. As described above, a significant clearance of aggregates in the capture step facilitates the subsequent purification steps in the process. It may even allow the use of feeds that would otherwise not be feasible for production due to too high aggregate contents.

The elution may be performed by using any suitable solution used for elution from Protein A media. In some embodiments the elution buffer or the elution buffer gradient comprises at least one anion species selected from the group consisting of acetate, citrate, glycine, succinate, phosphate, and formiate.

In certain embodiments the elution buffer or the elution buffer gradient comprises at least one elution additive, such as arginine or urea. The use of such additives can further increase the pH levels for elution of the Fc-containing protein.

In some embodiments, the eluate of step f) is collected in a pool and the pH of said pool is at least 0.5 pH units higher than the pH of said elution buffer or the pH of said elution buffer gradient at the end of step e). The pH level of the pool can be at least 4.5, such as at least 5.0 or at least 5.5 or between 4.5 and 6.5 or between 5.0 and 6.5. A high pH level in the pool is important in order to prevent aggregate formation from the eluted monomeric Fc-containing protein, as the protein is exposed to the pool conditions for significant periods of time (at least several hours).

In some embodiments the method further comprises a step h), optionally performed after step g), wherein the matrix is cleaned by application of an alkaline solution of pH 13-14, such as a solution comprising 0.1 M to 0.5 M sodium hydroxide. As discussed earlier, for either SpA (domain E, D, A, B, C) or protein Z ligand, when at least one asparagine residue is mutated to an amino acid other than glutamine or aspartic acid, affinity media including these mutant ligands can better withstand cleaning procedures using alkaline agents (US patent application 2005/0143566). The increased stability means that the mutated protein's initial affinity for immunoglobulin is essentially retained for a prolonged period of time. Thus its binding capacity will decrease more slowly than that of the parental molecule in an alkaline environment. The environment can be defined as alkaline, meaning of an increased pH-value, for example above about 10, such as up to about 13 or 14, i.e. from 10-13 or 10-14, in general denoted alkaline conditions. Alternatively, the conditions can be defined by the concentration of NaOH, which can be up to about 1.0 M, such as 0.7 M or specifically about 0.5 M, accordingly within a range of 0.7-1.0 M.

Thus, the affinity to immunoglobulin i.e. the binding properties of the ligand, in the presence of the asparagine mutation as discussed, and hence the capacity of the matrix, is not essentially changed in time by treatment with an alkaline agent. Conventionally, for a cleaning in place treatment of an affinity separation matrix, the alkaline agent used is NaOH and the concentration thereof is up to 0.75 M, such as 0.5 M. Thus, its binding capacity will decrease to less than about 70%, preferably less than about 50% and more preferably less than about 30%, such as about 28%, after treatment with 0.5 M NaOH for 7.5 h.

In certain embodiments the method further comprises a step i) of applying said eluate or pool to a cation exchange resin without any adjustment of the pH of said eluate or pool. As the eluate (and thus the pool) produced by the method of invention is higher than for conventional protein A media, it is possible to apply the eluate/pool directly to a cation exchanger without any intermediate pH adjustment. This simplifies the process and allows for straight-through processing.

In some embodiments the method further comprises, before step i), a step of solvent-detergent virus inactivation. The two commonly used virus inactivation methods are low pH inactivation and solvent-detergent inactivation. As exposure to low pH causes aggregation, it is less desirable with the current method which enables separation without exposing the protein to low pH. However, solvent-detergent inactivation is amenable to application on the pool/eluate before application to e.g. a cation exchange step. In this method a detergent (e.g. 0.3-1.5% of a nonionic surfactant like Triton™ X-100 from Dow Chemical or Tween™ 80 from Uniqema) and a solvent (e.g. 0.1-0.5% tri n-butyl phosphate) are applied to the eluate/pool and allowed to act for 30-90 min, such as about 45 min.

The present invention relates to a method of isolating an immunoglobulin, such as IgG, IgA and/or IgM, wherein a ligand or a matrix according to the invention is used. Thus, the invention encompasses a process of chromatography, wherein at least one target compound is separated from a liquid by adsorption to a ligand or matrix described above. The desired product can be the separated compound or the liquid. Thus, this aspect of the invention relates to affinity chromatography, which is a widely used and well-known separation technique. In brief, in a first step, a solution comprising the target compounds, preferably antibodies as mentioned above, is passed over a separation matrix under conditions allowing adsorption of the target compound to ligands present on said matrix. Such conditions are controlled e.g. by pH and/or salt concentration i.e. ionic strength in the solution. Care should be taken not to exceed the capacity of the matrix, i.e. the flow should be sufficiently slow to allow a satisfactory adsorption. In this step, other components of the solution will pass through in principle unimpeded.

In a fourth aspect the invention discloses a method of selecting an elution buffer for a matrix according to any embodiment described above, with an adsorbed Fc-containing protein, comprising the steps of:
a) providing a solution comprising an Fc-containing protein and at least one other substance;
b) contacting said solution with said separation matrix under conditions where the Fc-containing protein and at least part of the other substance adsorb to the separation matrix;
c) optionally washing said separation matrix with at least one wash buffer;
d) eluting said separation matrix with an elution buffer gradient of decreasing pH, wherein at least part of said elution buffer gradient is within the pH range of 6.0-4.0;
e) measuring the content of said Fc-containing protein and said other substance in the eluate obtained in step d) and;
f) selecting an elution buffer having the pH of the buffer gradient where at least 90%, such as at least 95% of the Fc-containing protein is eluted and where less than 25%, such as less than 10% of the adsorbed other substance is eluted.

In certain embodiments the other substance comprises host cell proteins, such as CHO cell proteins, or aggregates of said Fc-containing protein.

EXAMPLES

Below, the present invention will be described by way of examples, which are provided for illustrative purposes only and accordingly are not to be construed as limiting the scope of the present invention as defined by the appended claims. All references given below and elsewhere in this application are hereby included herein by reference.

Mutagenesis of Protein

Site-directed mutagenesis was performed by a two-step PCR using oligonucleotides coding for the defined amino acid replacement. As template a plasmid containing a single domain of either wild type Z (SEQ ID NO: 6) or mutated Z (to create two or more mutations) was used. The PCR fragments were ligated into an E. coli expression vector (pGO). DNA sequencing was used to verify the correct sequence of inserted fragments.

To form multimers of Z(H18E), Z(H18del), Z(H18S, P57I), Z(H18S,N28A) and Z(H18S,N28A,P57I) an Acc I site located in the starting codons (GTA GAC) of the C or Z domain was used, corresponding to amino acids VD. pGO Z(H18E)1, pGO Z(H18del)1, pGO Z(H18S,P57I)1, pGO Z(H18S,N28A)1 and pGO Z(H18S,N28A,P57I)1 were digested with Acc I and CIP treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.→25° C. in 45 min) in ligation buffer. The resulting product consists approximately to ¼ of fragments likely to be ligated into an Acc I site (correct PCR fragments and/or the digested vector). After ligation and transformation colonies were PCR screened to identify constructs containing Z(H18E)2, Z(H18del)2, Z(H18S, P57I)4, Z(H18S,N28A)4 and Z(H18S,N28A,P57I)4. Positive clones were verified by DNA sequencing.

Construct Expression and Purification

The constructs were expressed in the bacterial periplasm by fermentation of E. coli K12 in standard media. After fermentation the cells were heat-treated to release the periplasm content into the media. The constructs released into the medium were recovered by microfiltration with a membrane having a 0.2 µm pore size.

Each construct, now in the permeate from the filtration step, was purified by affinity. The permeate was loaded onto a chromatography medium containing immobilized IgG. The loaded product was washed with phosphate buffered saline and eluted by lowering the pH.

The elution pool was adjusted to a neutral pH and reduced by addition of dithiothreitol. The sample was then loaded onto an anion exchanger. After a wash step the construct was eluted in a NaCl gradient to separate it from any contaminants. The elution pool was concentrated by ultrafiltration to 40-50 mg/ml.

The purified ligands were analyzed with LC-MS to determine the purity and to ascertain that the molecular weight corresponded to the expected (based on the amino acid sequence).

The mutant Z(H18del)2 (SEQ ID NO: 10) did not bind to the IgG medium in the affinity step. Hence it was concluded that this mutation caused a loss of the IgG-binding capability and no further experiments were made with H18del mutants.

Activation

The base matrix used was rigid crosslinked agarose beads of 85 microns average diameter, prepared according to the methods of U.S. Pat. No. 6,602,990 and with a pore size corresponding to an inverse gel filtration chromatography Kay value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750. All buffers used in the experiments had been degassed by nitrogen gas for at least 5-10 min.

After immobilisation the gels were washed 3×GV with distilled water. The gels+1 GV {0.1 M phosphate/1 mM EDTA/10% thioglycerol pH 8.6} was mixed and the tubes were left in a shaking table at room temperature over night. The gels were then washed alternately with 3×GV {0.1 M TRIS/0.15 M NaCl pH 8.6} and 0.5 M HAc and then 8-10×GV with distilled water. Gel samples were sent to an external laboratory for amino acid analysis and the ligand content (mg/ml gel) was calculated from the total amino acid content.

Example 1

Prototypes

Mutant Z(H18E)2 (SEQ ID NO: 9): ligand dimers containing two copies of protein Z, each containing the H18E substitution (Z(H18E)2), with ligand density of 5.2 mg/ml.

Comparative prototype Z2 (similar to SEQ ID NO: 9, expect H18 are not substituted to E): ligand dimer containing two copies of protein Zvar2 (Z2), with ligand density of 5.9 mg/ml.

Mutant Z(H18S,P57I)4 (SEQ ID NO: 11): ligand tetramer containing four copies of protein Z, each containing the H18S,P57I substitutions Z(H18S,P57I)4, with ligand density of 5.3 mg/ml.

Mutant Z(H18S,N28A)4 (SEQ ID NO: 12): ligand tetramer containing four copies of protein Z, each containing the H18S,N28A substitutions, with ligand density of 6.9 mg/ml.

Comparative prototype Z4 (similar to SEQ ID NO: 11, expect H18 and P57 are not substituted to S and I respectively): ligand tetramer containing four copies of protein Zvar2 (Z2), with ligand density of 6.0 mg/ml.

Comparative prototype Z(H18S)4 (similar to SEQ ID NO:12, except N28 is not substituted to A): ligand tetramer containing four copies of protein Z, each containing the H18S substitution, with ligand density of 6.7 mg/ml.

Comparative prototype Z(N28A)4 (similar to SEQ ID NO:12, except H18 is not substituted to S): ligand tetramer containing four copies of protein Z, each containing the N28A substitution, with ligand density of 7.7 mg/ml.

For each prototype, 2 ml of resin was packed in Tricorn 5 100 column.

Protein

Gammanorm 165 mg/ml (Octapharma), diluted to 1 mg/ml in Equilibration buffer.

Equilibration Buffer

APB Phosphate buffer 20 mM+0.15 M NaCl, pH 7.4 (Elsichrom AB)

Elution Buffers

Citrate buffer 0.1 M, pH 6.

Citrate buffer 0.1 M, pH 3.

CIP 0.1 M NaOH.

Experimental Details and Results:

The breakthrough capacity was determined with an ÄKTAExplorer 10 system at a residence time of 2.4 minutes. Equilibration buffer was run through the bypass column until a stable baseline was obtained. This was done prior to auto zeroing. Sample was applied through the bypass until the 100% UV signal was obtained. Then, equilibration buffer was applied to the column again until a stable baseline was obtained. Sample was loaded onto the column until a UV signal of 85% of maximum absorbance was reached. The column was then washed with equilibration buffer until a UV signal of 20% of maximum absorbance at flow rate 0.5 ml/min. The protein was eluted with a linear gradient over 10 column volumes starting at pH 6.0 and ending at pH 3.0 at a flow rate of 0.5 ml/min. Then the column was cleaned with 0.1 M NaOH at flow rate 0.5 ml/min and re-equilibrated with equilibration buffer prior to adding 20% ethanol. The last step was to check the sample concentration by loading sample through the bypass column until a 100% UV signal was obtained.

For calculation of breakthrough capacity at 10%, equation below was used. That is i.e. the amount of IgG that is loaded onto the column until the concentration of IgG in the column effluent is 10% of the IgG concentration in the feed.

$$q_{10\%} = \frac{C_0}{V_C}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;

$A_{sub}$=absorbance contribution from non-binding IgG subclass;

$A(V)$=absorbance at a given applied volume;

$V_c$=column volume;

$V_{app}$=volume applied until 10% breakthrough;

$V_{sys}$=system dead volume;

$C_0$=feed concentration.

The dynamic binding capacity (DBC) at 10% breakthrough was calculated and the appearance of the curve was studied. The curve was also studied regarding binding, elution and CIP peak. The dynamic binding capacity (DBC) was calculated for 5, 10 and 80% breakthrough. Some results are shown in Table 1. Similar capacity was observed for ligands with H18S substitution as compared to the parental H18 ligand (Z2 or Z4).

IgG capacity and elution study for polyclonal human IgG and different mABs were done on Z(H18E)2, Z(H18S,P57I) 4, Z(H18S,N28A)4, Z2 and Z4. Some examples are shown in Table 1.

TABLE 1

Capacity data for Z(H18E)2, Z(H18S, N28A)4, Z(H18S, P57I)4, Z2 and Z4, using 1 mg/ml IgG dissolved in 20 mM PBS + 0.15M NaCl buffer, pH 7.4.

| prototype | Qb10% (mg/ml resin) | Qb80% (mg/ml resin) | Residence time (min) | Ligand density (mg/ml) |
|---|---|---|---|---|
| Z(H18S, N28A)4 | 35.2 | 56.0 | 2.4 | 6.9 |
| Z(H18S, N28A)4 | 45.9 | 59.1 | 6 | 6.9 |
| Z(H18S, P57I)4 | 35.6 | 56.0 | 2.4 | 5.3 |
| Z(H18S, P57I)4 | 47.0 | 58.0 | 6 | 5.3 |
| Z(H18S)4 | 37.0 | 62.2 | 2.4 | 6.7 |
| Z(H18S)4 | 55.0 | 67.5 | 6 | 6.7 |
| Z(N28A)4 | 37.4 | 62.5 | 2.4 | 7.7 |
| Z(N28A)4 | 53.2 | 65.6 | 6 | 7.7 |
| Z(H18E)2 | 26.6 | 41.3 | 2.4 | 5.2 |
| Z(H18E)2 | 31.6 | 43.3 | 6 | 5.2 |
| Z2 | 31.4 | 43.8 | 2.4 | 5.9 |
| Z2 | 40.4 | 47.1 | 6 | 5.9 |
| Z4 | 36.7 | 54.4 | 2.4 | 6.0 |
| Z4 | 48.0 | 57.2 | 6 | 6.0 |

The elution studies were done for different cell culture supernatant (mAb C, mAb D) or polyclonal human IgG in phosphate buffer. The elution pH increases with 0.6 to 1.8 pH units for Z(H18E)2, Z(H18S,P57I)4 and Z(H18S, N28A)4 compared to Z2 and Z4. The biggest difference is shown with polyclonal IgG (Gammanorm) while the mAb D shows somewhat smaller differences. In these elution studies approximately 10 mg cell culture supernatant (different cell culture supernatants were used, see Table 2) was loaded on the column. A gradient elution from pH 6 to pH 3 was done using 0.1 M citrate buffers. The pH at peak apex was noted (see Table 2.)

TABLE 2

Elution pH for polyclonal human IgG and two different mAbs.

| prototype | pH hIgG (first peak) | pH hIgG (second peak) | pH mAb |
|---|---|---|---|
| Z(H18S, N28A)4 | 5.68 | 5.15 | 5.05 |
| Z(H18S, P57I)4 | 5.44 | 4.91 | 4.71 |
| Z(H18S)4 | 5.10 | 4.61 | |
| Z(N28A)4 | 4.77 | 4.42 | |
| Z(H18E)2 | 4.83 | 4.23 | 4.48 |
| Z2 | 3.99 | 3.59 | 4.03 |
| Z4 | 3.89 | 3.53 | 4.12 |

Note
pH hIgG (first peak) and pH hIgG (second peak) are polyclonal IgG (Gammanorm).

Figure 3:
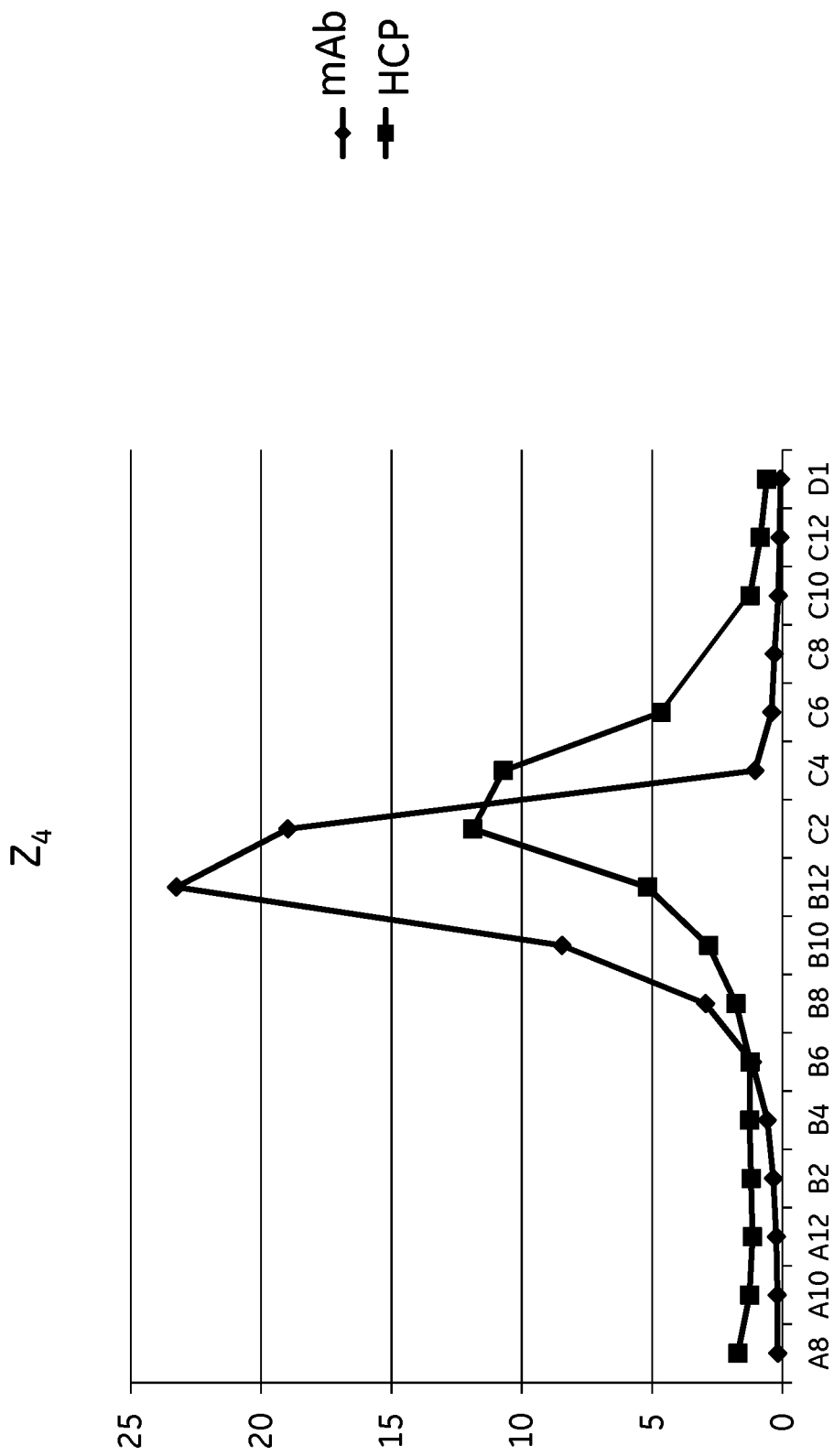
FIG. 3 shows an overlay of the pH-gradient elution chromatograms of monoclonal antibody and host cell proteins for comparative prototype Z4.

Except for higher elution pH for Z(H18E)2, Z(H18S, P57I)4 and Z(H18S,N28A)4, they also have better separation properties than Z2 and Z4. FIGS. 2 and 3 show the elution of antibody E and adsorbed host cell proteins from Z4 (FIG. 3) and Z(H18S,P57I)4 (FIG. 2) in a decreasing pH gradient. On Z4 (as well as on other matrices not having the H18 mutations), the antibody and the HCP co-elute, meaning that HCP bound to the matrix will not be removed in the chromatography step. On Z(H18S,P57I)4 the HCP elutes later in the gradient, which creates a possibility for selective elution to remove the bound HCP, either by gradient elution or by applying an elution buffer having a pH where the antibody elutes and then e.g. applying a stripping buffer at lower pH to remove the HCP.

Figure 4:
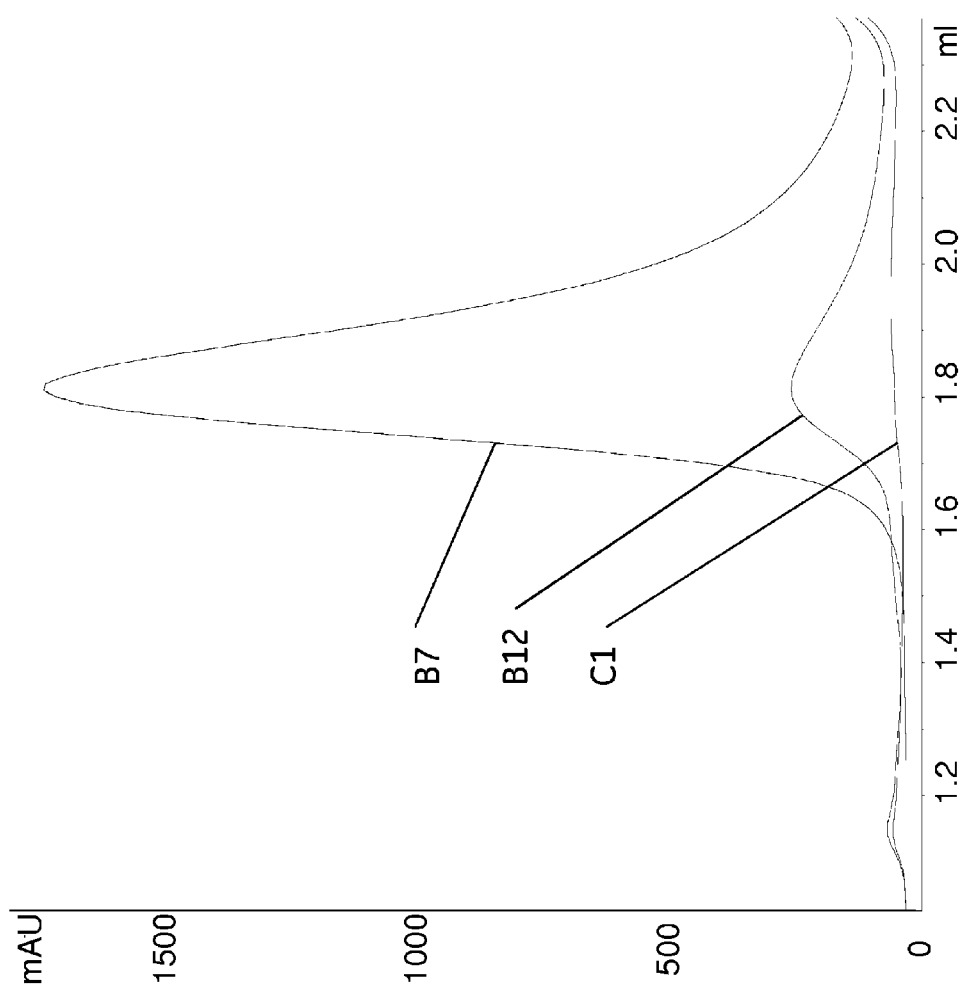
FIG. 4 is an overlay of representative chromatogram showing results for size exclusion chromatography on the mAb fractions B7, B12 and C2 from the experiment with Z(H18S,P57I)4 described in FIG. 2.

Also antibody aggregates elute at a lower pH than the antibody monomer, as illustrated by FIG. 4. This figure shows SEC chromatograms for the eluate fractions of a monoclonal antibody on Z(H18S,P57I)4 (the same fractions as shown in FIG. 2). It can be seen that the main antibody peak (fraction B7) contains no aggregates, while the aggregates start to appear in B12 and the later fraction C1 consists almost entirely of aggregates.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

The invention claimed is:

1. An immunoglobulin-binding protein comprising one or more mutated immunoglobulin-binding domains (monomers) of staphylococcal Protein A (E, D, A, B, C) or protein Z,
   wherein in at least one of the one or more mutated monomers the amino acid sequence of the monomer is defined by SEQ ID NO: 14, 16, 17, or 18.

2. The protein of claim 1, wherein the protein comprises one or more mutated monomers defined by SEQ ID NO: 14.

3. The protein of claim 1, wherein the protein comprises one or more mutated monomers defined by SEQ ID NO: 16.

4. The protein of claim 1, wherein the protein comprises one or more mutated monomers defined by SEQ ID NO: 17.

5. The protein of claim 1, wherein the protein comprises one or more mutated monomers defined by SEQ ID NO: 18.

6. The protein of claim 1, wherein the protein comprises amino acid sequence defined by SEQ ID NO: 9.

7. The protein of claim 1, wherein the protein comprises amino acid sequence defined by SEQ ID NO: 11 or 12.

8. The protein of claim 1, comprising at least two mutated monomers.

9. The protein of claim 1, comprising 3, 4, 5 or 6 monomers.

10. The protein of claim 1, further comprising a C-terminal cysteine.

11. An affinity separation matrix, comprising the protein of claim 1 coupled to a support.

12. The matrix of claim 11, comprising 5-15 mg/ml of said protein coupled to said support.

13. The matrix of claim 11, wherein said protein is coupled to the support via a thioether bridge.

14. The matrix of claim 11, wherein said protein is coupled via a C-terminal cysteine.

15. The matrix of claim 11, comprising 6-11 mg/ml of said protein coupled to said support.

16. The matrix of claim 11, wherein said support comprises a polysaccharide.

17. The matrix of claim 11, wherein said support is crosslinked with hydroxyalkyl ether crosslinks.

18. The matrix of claim 11, wherein said support comprises a polyhydroxy polymer.

19. The matrix of claim 11, wherein said support comprises agar or agarose.

20. The matrix of claim 11, wherein said support is crosslinked.

21. A method of separating Fc-containing proteins from other substances, comprising the steps of:
 a) providing an affinity separation matrix of claim 11;
 b) providing a solution comprising an Fc-containing protein and at least one other substance;
 c) contacting said solution with said separation matrix;
 d) optionally washing said separation matrix with at least one wash buffer;
 e) eluting said separation matrix with an elution buffer, or an elution buffer gradient of decreasing pH, to obtain an eluate comprising said Fc-containing protein and;
 f) recovering said eluate
 wherein said elution buffer has a pH of 4.0-6.0 or wherein at least part of said elution buffer gradient is within the pH range of 6.0-4.0.

22. The method of claim 21, further comprising a step g) of stripping said separation matrix with a stripping buffer having a pH of a least 0.1 pH units lower than the pH of the elution buffer or the pH of the elution buffer gradient at the end of step e).

23. The method of claim 22, further comprising a step h), optionally performed after step g), wherein the matrix is cleaned by application of an alkaline solution of pH 13-14.

24. The method of claim 22, further comprising a step i) of applying said eluate or pool to a cation exchange resin without any adjustment of the pH of said eluate or pool.

25. The method of claim 24, further comprising before step i) a step of solvent-detergent virus inactivation.

26. The method of claim 22, wherein said solution comprises host cell proteins including CHO cell or *E. coli* proteins that are desorbed during step g).

27. The method of 22, wherein said solution comprises at least 5% aggregates of said Fc-containing protein calculated on the total amount of the Fc-containing protein in said solution, wherein aggregates are desorbed during step g), and wherein the aggregate content in the recovered eluate is less than 1% calculated on the total amount of the Fc-containing protein in said recovered eluate.

28. The method of claim 22, further comprising a step h), optionally performed after step g), wherein the matrix is cleaned by application of an 0.1 M to 0.5 M sodium hydroxide solution of pH 13-14.

29. The method of claim 22, wherein said solution comprises host cell proteins.

30. The method of claim 29, wherein host cell proteins are desorbed during step g).

31. The method of 22, wherein said solution comprises at least 1% aggregates of said Fc-containing protein calculated on the total amount of the Fc-containing protein in said solution.

32. The method of claim 31, wherein aggregates are desorbed during step g).

33. The method of claim 32, wherein the aggregate content in the recovered eluate is less than 1%, calculated on the total amount of the Fc-containing protein in said recovered eluate.

34. The method of claim 32, wherein the aggregate content in the recovered eluate is less than 0.5% calculated on the total amount of the Fc-containing protein in said recovered eluate.

35. The method of claim 32, wherein the aggregate content in the recovered eluate is less than 0.2% calculated on the total amount of the Fc-containing protein in said recovered eluate.

36. The method of 22, wherein said solution comprises at least 10% aggregates of said Fc-containing protein calculated on the total amount of the Fc-containing protein in said solution, wherein aggregates are desorbed during step g), and wherein the aggregate content in the recovered eluate is less than 1% calculated on the total amount of the Fc-containing protein in said recovered eluate.

37. The method of claim 21, wherein said elution buffer or said elution buffer gradient comprises at least one anion species selected from the group consisting of acetate, citrate, glycine, succinate, phosphate, and formiate.

38. The method of claim 21, wherein said elution buffer or said elution buffer gradient comprises at least one elution additive.

39. The method of claim 21, wherein in step f), the eluate is collected in a pool and the pH of said pool is at least 0.5 pH units higher than the pH of said elution buffer or the pH of said elution buffer gradient at the end of step e).

40. The method of claim 21, wherein said elution buffer or said elution buffer gradient comprises at least arginine or urea as elution additive.

* * * * *

SEQUENCE LISTING

<160> NUMBER OF SEQ ID NOS: 18

<210> SEQ ID NO 1
<211> LENGTH: 56
<212> TYPE: PRT
<213> ORGANISM: Staphylococcus aureus

<400> SEQUENCE: 1

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55

<210> SEQ ID NO 2
<211> LENGTH: 61

```
<212> TYPE: PRT
<213> ORGANISM: Staphylococcus aureus

<400> SEQUENCE: 2

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
50                  55

<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
50                  55

<210> SEQ ID NO 6
```

<211> LENGTH: 58
    <212> TYPE: PRT
    <213> ORGANISM: Escherichia coli

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
    <211> LENGTH: 58
    <212> TYPE: PRT
    <213> ORGANISM: Escherichia coli

<400> SEQUENCE: 7

Val Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
    <211> LENGTH: 58
    <212> TYPE: PRT
    <213> ORGANISM: Escherichia coli

<400> SEQUENCE: 8

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 9
    <211> LENGTH: 117
    <212> TYPE: PRT
    <213> ORGANISM: Escherichia coli

<400> SEQUENCE: 9

Val Asp Ala Lys Phe Asp Lys Glu Gln Gln Asn Ala Phe Tyr Glu Ile
1               5                   10                  15

Leu Glu Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Ala Lys Phe Asp
    50                  55                  60

Lys Glu Gln Gln Asn Ala Phe Tyr Glu Ile Leu Glu Leu Pro Asn Leu

-continued

```
                65                  70                  75                  80
Thr Glu Glu Gln Arg Asn Ala Phe Ile Gln Ser Leu Lys Asp Asp Pro
                    85                  90                  95

Ser Gln Ser Ala Asn Leu Leu Ala Glu Ala Lys Lys Leu Asn Asp Ala
                100                 105                 110

Gln Ala Pro Lys Cys
            115

<210> SEQ ID NO 10
<211> LENGTH: 115
<212> TYPE: PRT
<213> ORGANISM: Escherichia coli

<400> SEQUENCE: 10

Val Asp Ala Lys Phe Asp Lys Glu Gln Gln Asn Ala Phe Tyr Glu Ile
1               5                   10                  15

Leu Leu Pro Asn Leu Thr Glu Glu Gln Arg Asn Ala Phe Ile Gln Ser
                20                  25                  30

Leu Lys Asp Asp Pro Ser Gln Ser Ala Asn Leu Leu Ala Glu Ala Lys
            35                  40                  45

Lys Leu Asn Asp Ala Gln Ala Pro Lys Val Asp Ala Lys Phe Asp Lys
        50                  55                  60

Glu Gln Gln Asn Ala Phe Tyr Glu Ile Leu Leu Pro Asn Leu Thr Glu
65                  70                  75                  80

Glu Gln Arg Asn Ala Phe Ile Gln Ser Leu Lys Asp Asp Pro Ser Gln
                85                  90                  95

Ser Ala Asn Leu Leu Ala Glu Ala Lys Lys Leu Asn Asp Ala Gln Ala
                100                 105                 110

Pro Lys Cys
        115

<210> SEQ ID NO 11
<211> LENGTH: 233
<212> TYPE: PRT
<213> ORGANISM: Escherichia coli

<400> SEQUENCE: 11

Val Asp Ala Lys Phe Asp Lys Glu Gln Gln Asn Ala Phe Tyr Glu Ile
1               5                   10                  15

Leu Ser Leu Pro Asn Leu Thr Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Ile Lys Val Asp Ala Lys Phe Asp
        50                  55                  60

Lys Glu Gln Gln Asn Ala Phe Tyr Glu Ile Leu Ser Leu Pro Asn Leu
65                  70                  75                  80

Thr Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
                100                 105                 110

Gln Ala Ile Lys Val Asp Ala Lys Phe Asp Lys Glu Gln Gln Asn Ala
            115                 120                 125

Phe Tyr Glu Ile Leu Ser Leu Pro Asn Leu Thr Glu Glu Gln Arg Asn
        130                 135                 140

Ala Phe Ile Gln Ser Leu Lys Asp Asp Pro Ser Gln Ser Ala Asn Leu
```

```
                145                 150                 155                 160
Leu Ala Glu Ala Lys Lys Leu Asn Asp Ala Gln Ala Ile Lys Val Asp
                    165                 170                 175

Ala Lys Phe Asp Lys Glu Gln Gln Asn Ala Phe Tyr Glu Ile Leu Ser
                180                 185                 190

Leu Pro Asn Leu Thr Glu Glu Gln Arg Asn Ala Phe Ile Gln Ser Leu
                195                 200                 205

Lys Asp Asp Pro Ser Gln Ser Ala Asn Leu Leu Ala Glu Ala Lys Lys
210                 215                 220

Leu Asn Asp Ala Gln Ala Ile Lys Cys
225                 230

<210> SEQ ID NO 12
<211> LENGTH: 232
<212> TYPE: PRT
<213> ORGANISM: Escherichia coli

<400> SEQUENCE: 12

Val Asp Ala Lys Phe Asp Lys Glu Gln Gln Asn Ala Phe Tyr Glu Ile
1               5                   10                  15

Leu Ser Leu Pro Asn Leu Thr Glu Glu Gln Arg Ala Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Val Asp Ala Lys Phe Asp
50                  55                  60

Lys Glu Gln Gln Asn Ala Phe Tyr Glu Ile Leu Ser Leu Pro Asn Leu
65                  70                  75                  80

Thr Glu Glu Gln Arg Ala Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys Val Asp Ala Lys Phe Asp Lys Glu Gln Gln Asn Ala
        115                 120                 125

Phe Tyr Glu Ile Leu Ser Leu Pro Asn Leu Thr Glu Glu Gln Arg Ala
130                 135                 140

Ala Phe Ile Gln Ser Leu Lys Asp Asp Pro Ser Gln Ser Ala Asn Leu
145                 150                 155                 160

Ala Glu Ala Lys Lys Leu Asn Asp Ala Gln Ala Pro Lys Val Asp Ala
                165                 170                 175

Lys Phe Asp Lys Glu Gln Gln Asn Ala Phe Tyr Glu Ile Leu Ser Leu
            180                 185                 190

Pro Asn Leu Thr Glu Glu Gln Arg Ala Ala Phe Ile Gln Ser Leu Lys
        195                 200                 205

Asp Asp Pro Ser Gln Ser Ala Asn Leu Leu Ala Glu Ala Lys Lys Leu
210                 215                 220

Asn Asp Ala Gln Ala Pro Lys Cys
225                 230

<210> SEQ ID NO 13
<211> LENGTH: 232
<212> TYPE: PRT
<213> ORGANISM: Escherichia coli

<400> SEQUENCE: 13

Val Asp Ala Lys Phe Asp Lys Glu Gln Gln Asn Ala Phe Tyr Glu Ile
```

```
            1               5                  10                 15
Leu Ser Leu Pro Asn Leu Thr Glu Glu Gln Arg Ala Ala Phe Ile Gln
                20                  25                 30

Ser Leu Lys Asp Asp Pro Ser Gln Ser Ala Asn Leu Leu Ala Glu Ala
                35                  40                 45

Lys Lys Leu Asn Asp Ala Gln Ala Ile Lys Val Asp Ala Lys Phe Asp
                50                  55                 60

Lys Glu Gln Gln Asn Ala Phe Tyr Glu Ile Leu Ser Leu Pro Asn Leu
 65                     70                 75                 80

Thr Glu Glu Gln Arg Ala Ala Phe Ile Gln Ser Leu Lys Asp Asp Pro
                    85                 90                 95

Ser Gln Ser Ala Asn Leu Leu Ala Glu Ala Lys Lys Leu Asn Asp Ala
                100                105                110

Gln Ala Ile Lys Val Asp Ala Lys Phe Asp Lys Glu Gln Gln Asn Ala
                115                120                125

Phe Tyr Glu Ile Leu Ser Leu Pro Asn Leu Thr Glu Glu Gln Arg Ala
130                 135                140

Ala Phe Ile Gln Ser Leu Lys Asp Asp Pro Ser Gln Ser Ala Asn Leu
145                 150                155                160

Ala Glu Ala Lys Lys Leu Asn Asp Ala Gln Ala Ile Lys Val Asp Ala
                165                170                175

Lys Phe Asp Lys Glu Gln Gln Asn Ala Phe Tyr Glu Ile Leu Ser Leu
                180                185                190

Pro Asn Leu Thr Glu Glu Gln Arg Ala Ala Phe Ile Gln Ser Leu Lys
                195                200                205

Asp Asp Pro Ser Gln Ser Ala Asn Leu Leu Ala Glu Ala Lys Lys Leu
                210                215                220

Asn Asp Ala Gln Ala Ile Lys Cys
225                 230
```

<210> SEQ ID NO 14
<211> LENGTH: 58
<212> TYPE: PRT
<213> ORGANISM: Escherichia coli

<400> SEQUENCE: 14

```
Val Asp Ala Lys Phe Asp Lys Glu Gln Gln Asn Ala Phe Tyr Glu Ile
 1               5                  10                 15

Leu Glu Leu Pro Asn Leu Thr Glu Glu Gln Arg Asn Ala Phe Ile Gln
                20                  25                 30

Ser Leu Lys Asp Asp Pro Ser Gln Ser Ala Asn Leu Leu Ala Glu Ala
                35                  40                 45

Lys Lys Leu Asn Asp Ala Gln Ala Pro Lys
                50                  55
```

<210> SEQ ID NO 15
<211> LENGTH: 57
<212> TYPE: PRT
<213> ORGANISM: Escherichia coli

<400> SEQUENCE: 15

```
Val Asp Ala Lys Phe Asp Lys Glu Gln Gln Asn Ala Phe Tyr Glu Ile
 1               5                  10                 15

Leu Leu Pro Asn Leu Thr Glu Glu Gln Arg Asn Ala Phe Ile Gln Ser
                20                  25                 30

Leu Lys Asp Asp Pro Ser Gln Ser Ala Asn Leu Leu Ala Glu Ala Lys
```

```
                35                  40                  45
Lys Leu Asn Asp Ala Gln Ala Pro Lys
    50                  55

<210> SEQ ID NO 16
<211> LENGTH: 58
<212> TYPE: PRT
<213> ORGANISM: Escherichia coli

<400> SEQUENCE: 16

Val Asp Ala Lys Phe Asp Lys Glu Gln Gln Asn Ala Phe Tyr Glu Ile
1               5                   10                  15

Leu Ser Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Ile Lys
    50                  55

<210> SEQ ID NO 17
<211> LENGTH: 58
<212> TYPE: PRT
<213> ORGANISM: Escherichia coli

<400> SEQUENCE: 17

Val Asp Ala Lys Phe Asp Lys Glu Gln Gln Asn Ala Phe Tyr Glu Ile
1               5                   10                  15

Leu Ser Leu Pro Asn Leu Thr Glu Glu Gln Arg Ala Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 18
<211> LENGTH: 58
<212> TYPE: PRT
<213> ORGANISM: Escherichia coli

<400> SEQUENCE: 18

Val Asp Ala Lys Phe Asp Lys Glu Gln Gln Asn Ala Phe Tyr Glu Ile
1               5                   10                  15

Leu Ser Leu Pro Asn Leu Thr Glu Glu Gln Arg Ala Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Ile Lys
    50                  55
```